United States Patent
Curtis et al.

(10) Patent No.: US 8,692,987 B2
(45) Date of Patent: Apr. 8, 2014

(54) ARTIFACT APPARATUS TO MIMIC REFLECTION LOSSES OF SOLUTION-FILLED MICROTITER PLATE READERS AND RELATED USES THEREOF

(75) Inventors: Richard H. Curtis, Gorham, ME (US); John Thomas Bradshaw, Gorham, ME (US)

(73) Assignee: Artel, Inc., Westbrook, ME (US)

( * ) Notice: Subject to any disclaimer, the term of this patent is extended or adjusted under 35 U.S.C. 154(b) by 172 days.

(21) Appl. No.: 13/206,261

(22) Filed: Aug. 9, 2011

(65) Prior Publication Data
US 2013/0038873 A1    Feb. 14, 2013

(51) Int. Cl.
*G01N 21/01*    (2006.01)

(52) U.S. Cl.
USPC ............................................. 356/244; 356/234

(58) Field of Classification Search
USPC ................................................. 356/243–244
See application file for complete search history.

(56) References Cited

U.S. PATENT DOCUMENTS

| | | | |
|---|---|---|---|
| 7,072,036 B2* | 7/2006 | Jones et al. | 356/246 |
| 7,448,258 B2* | 11/2008 | Saunders et al. | 73/73 |
| 2002/0131047 A1* | 9/2002 | Zarrabian et al. | 356/454 |
| 2003/0030797 A1* | 2/2003 | Palladino et al. | 356/243.1 |

* cited by examiner

Primary Examiner — Tarifur Chowdhury
Assistant Examiner — Isiaka Akanbi
(74) Attorney, Agent, or Firm — Chris A. Caseiro

(57) ABSTRACT

An apparatus used to calibrate microtiter plate readers. The apparatus includes one or more structures having two exterior surfaces wherein one of the exterior surfaces is coated with a coating selected to establish on that surface a reflection loss that mimics reflection loss at an air-liquid interface, and the other of the two exterior surfaces is coated with a coating selected to establish a reflection loss on that surface that mimics the reflection loss at a bottom surface of a microtiter plate. The apparatus may be a single layer, a multi-layered composition or a container. The apparatus is an artifact that may be used to calibrate a plate reader by mimicking a solution-filled microtiter plate. The artifact may be used for a plurality of liquids, including water. The artifact produces reflection losses more closely mirroring reflection losses expected for a liquid-filled microtiter plate well.

19 Claims, 1 Drawing Sheet

ARTIFACT APPARATUS TO MIMIC REFLECTION LOSSES OF SOLUTION-FILLED MICROTITER PLATE READERS AND RELATED USES THEREOF

BACKGROUND OF THE INVENTION

1. Field of the Invention

The present invention relates to an apparatus to address reflection losses associated with microtiter plate readers. More particularly, the present invention relates to modified calibration artifacts for the purpose of calibrating and/or monitoring the calibration of, microtiter plate readers.

2. Description of the Prior Art

Microtiter plate readers are a form of absorbance measuring spectrophotometer, adapted to make their readings vertically through the wells of a microtiter plate containing liquid. Typically, the wells of the microtiter plate are open at the top, so the beam enters (or exits depending on the design) through an air-liquid interface. The bottoms of the wells may be plastic or glass, depending on the design. Thus, as a light beam traverses the microtiter plate, it passes through three interfaces on the way through: air-liquid at the top surface, liquid-solid at the inside bottom of the well and solid-air at the outside of the bottom of the well. This differs from a cuvette in a horizontal beam spectrophotometer which necessarily has four interfaces through which the beam travels. This difference is one of the reasons for discrepancy between readings made in a cuvette using a horizontal beam and a microtiter plate using a vertical beam.

Other reasons for differences in readings between spectrophotometer and plate reader are more related to economy of design and speed of reading. Microtiter plates contain a multiplicity of wells, generally at least 96, so the readers are configured to make their readings quickly to minimize overall read time, sometimes leading to compromises in the optical design and accuracy of results. For one group of readers tested, the results of measurements at A=0.2 in a microtiter plate varied between readers and between channels of readers by up to 8%, a variability far greater than would ordinarily be found in readings of different spectrophotometers. Such differences may be too great to reconcile a true reading and, therefore, exceed an established accuracy specification. In particular, it may negatively impact any comparison made between any two spectrophotometers or any two channels of a multichannel reader.

In an absorbance measuring plate reader, a collimated beam of light is directed (usually downward) onto a plate. A portion passes through the plate and is detected by a detector usually under the plate. Wavelength selection can occur by filter or monochromator and take place either above or below the plate. Some of the light is invariably lost from the beam as it passes through the plate. In addition to the absorbance taking place in the plate or its contents, some of the incident light is lost from the beam because it is reflected at each interface between different optical media. The reflected light will be directed upward back toward the source. In the ideal case, none of the reflected light winds up in the detector. In the case where the plate contents do not absorb, the "absorbance" of the plate as measured by the reader is actually a misnomer, because the light is not absorbed, merely removed from the original beam.

The intensity of light reflected from the boundary between two plane optical surfaces was theoretically derived by Augustin-Jean Fresnel in 1821. The relationship has been experimentally confirmed countless times since then, and holds under a wide range of conditions. In the simplest case, that of a well collimated beam of unpolarized light falling normally (at right angles) to a surface, the amount of light reflected at that surface is given by:

$$R = \left(\frac{n_1 - n_2}{n_1 + n_2}\right)^2 \qquad (1.1)$$

The quantities $n_i$ are the indices of refraction of light on either side of the boundary. The index of refraction is the ratio of the speed of light in the medium compared to that in vacuum. The reflection is the same whether the light is going one way through the boundary or the other. The balance of the beam of light (the part not reflected) is transmitted through the boundary and continues onward. In the case of normal incidence, the transmitted beam is also normal to the surface.

The reflections that naturally occur at all interfaces in a spectrophotometer can result in measurement errors. It is known in the art that multiple reflections of light from cuvette walls can cause errors in absorbance measurement results. Reflections occur from the various optical elements in the instrument and from the sample container. In a high quality spectrophotometer, the optical elements of the instrument are either anti-reflection coated to avoid reflections, or angled to direct reflections away from the detector. This leaves the sample as the principle source of reflection error. The reflections which lead to error are those which pass through the sample three times before reaching the detector. This occurs via the multiple reflection path from the exterior surface of the exit side of the sample, back to the exterior of the input side, and back again through the exit to the detector. In this case, the errors due to reflection will typically amount to about 0.3% at low absorbances, where the largest influence of reflection errors occurs for small absorbance readings (typically <0.5).

In some plate readers, the errors due to reflections are many times greater than this, due to compromises in the optical design to increase the throughput and decrease the cost. For instance, if the detector is: a) close to the microtiter plate, b) made of silicon, as most are, or c) normal to the beam axis, then it will reflect about 30% of the light incident on it back toward the plate. This back reflected light has the opportunity to be multiply reflected and wind up being detected after three passes through the sample. This component of reflected light which makes three passes through the sample before detection is what causes reflection errors in the results. The magnitude of each contribution to the three-pass multiple reflection paths are generally dictated by the types of surfaces present. Thus, the reflections from a cuvette are quite different from the reflections associated with a microtiter plate filled with water, for example, dependent upon the indices of refraction of the different layers described herein.

Attempts have been made to compensate for differences between plate readers. For example, U.S. Pat. No. 7,061,608 describes the use of special cuvettes as artifacts. The entire content of that patent is incorporated herein by reference. However, the special cuvettes may not be sufficient to compensate for reflection loss differences that exist between the cuvette and a sample-filled microtiter plate. These special cuvettes also may not be sufficient to compensate for the different reflection losses experienced among all types of different plate readers provided by multiple manufacturers. Therefore, what is needed is an artifact apparatus to address the difference in reflection losses between a cuvette and a solution-filled microtiter plate. This artifact should be applicable across a plurality of plate reader designs. In particular, what is needed is an artifact apparatus that may be used to calibrate and/or monitor a spectrophotometer by accounting for those reflection losses as a function of the liquid used in calibration solutions.

SUMMARY OF THE INVENTION

It is an object of the present invention to provide an artifact apparatus that has reflection loss properties similar to a microtiter plate filled with solution. It is also an object of the present invention to provide an artifact apparatus to address reflection losses across a plurality of plate reader designs. It is also an object of the present invention to provide an artifact apparatus to mimic reflection losses for such plate readers when measuring a microtiter plate filled with solution. Further, it is an object of the present invention to provide for the calibration and/or monitoring of plate readers using such an artifact apparatus, including for calibration solutions such as water and DMSO, or any other calibration solution of interest.

These and other objects are achieved by the present invention, which is a calibration artifact apparatus and one or more related uses of the artifact apparatus. The calibration artifact apparatus is adapted to mimic the reflection losses of a microtiter plate filled with liquid. A first embodiment of the invention is a unitary structure configured to mimic reflection losses representative of air-to-solid and air-to-liquid interfaces. The single structure is sufficiently transparent to allow light to pass therethrough. It may be glass or other material including, but not limited to, a nonmetallic material such as plastic. A second embodiment of the invention is a multi-layer structure configured to mimic reflection losses representative of air-to-solid and air-to-liquid interfaces. The multi-layer structure is sufficiently transparent to allow light to pass therethrough. Each layer of the multi-layer structure may be glass or other material including, but not limited to, a nonmetallic material such as plastic. A third embodiment of the invention is a container, such as a cuvette, vial or other fluid holding structure with opposing surfaces, wherein the opposing surfaces, respectively, mimic reflection losses associated with air-to-solid and air-to-liquid interfaces. The container is sufficiently transparent at the opposing surfaces to allow light to pass therethrough. The transparent areas of the container may be formed of glass or other material including, but not limited to, a nonmetallic material such as plastic. The result with any of these embodiments is an artifact that should produce the same reflection characteristics as that of a microtiter plate filled with a liquid such as water, DMSO, or any other liquid for which absorbance measurements are performed. It is to be noted that the third interface described herein, that of the solid-to-liquid interface at the inside bottom of the well, produces reflection losses of the light beam traversing the plate that are negligible relative to the reflection losses associated with the other two interfaces. Nevertheless, it is an option to consider accounting for the reflection losses at the solid-to-liquid interface through additional modification of the artifact apparatus of the present invention, in which the artifact apparatus is formed to mimic such losses as well. For example, an intermediate layer may be adapted to mimic such losses.

For the first and second embodiments of the invention, a first exterior surface of the artifact is adapted to have a reflection loss similar to that of an air-solid interface, thereby mimicking the bottom surface of a microtiter plate. The solid may be of the type used to contain a solution. A second exterior surface of the artifact is adapted to have a reflection loss similar to that of an air-liquid interface, thereby mimicking the interface for the liquid in a microtiter well. The second embodiment may be formed of two or more layers, wherein a first exterior layer includes an exterior surface possessing the reflection characteristics of solid-air, and a second exterior layer includes an exterior surface possessing the reflection characteristics of liquid-air. One or more interior layers may be positioned between the two exterior layers. If there is a plurality of middle layers, each may be of the same or a different configuration. Each may be formed of a material that absorbs light. One or more of the middle layer(s) may be neutral density glass, specifically designed optical interference material producing an output similar in spectral response to a dye material of interest, or a combination thereof. That is, it may function as an interference filter, with outer surfaces manufactured to mimic the reflection losses attributed to the bottom surface of a microtiter plate and the surface of an air-liquid interface.

For the third embodiment of the invention, the container includes a first surface adapted to have a reflection loss similar to that of an air-solid interface, thereby mimicking the bottom surface of a microtiter plate. The solid is of the type used to form a container to hold a solution to be tested. The solid may be plastic or glass. A second surface of the container is adapted to have a reflection loss similar to that of an air-liquid interface, thereby mimicking the solution in a microtiter well. The benefit of the container embodiment is that it allows for filling the container with a dye solution of interest. This allows for calibration of the plate reader using the same dye as may be used for calibration testing of a plate reader.

The artifact apparatus of the present invention may be used for calibration purposes in association with a horizontal beam spectrophotometer or a vertical beam spectrophotometer. It may be used in a spectrophotometer known to be calibrated to establish calibration information for the artifact. Once that calibration information is acquired, the artifact apparatus may be used in another spectrophotometer either for the purpose of calibrating that spectrophotometer, or to monitor the spectrophotometer to ensure it operates in a designated tolerance range. The artifact apparatus mimics reflection losses associated with solution-filled microtiter plates, and thereby accounts for them in determining the calibration of a spectrophotometer. The artifact may be designed to mimic a specific solution, such as water, DMSO or another liquid of interest. The artifact, in effect, "looks like" a solution filled microtiter plate. A plate reader can be more accurately calibrated because the calibration tool has not removed the different amounts of reflected light experienced between prior calibration devices and samples that are actually measured. In other words, the prior calibration devices gave one level of reflection loss and the samples gave a different reflection loss because of the different interfaces noted above. This difference shows up as an erroneous absorbance result in the sample. The present artifact more accurately represents the reflection losses occurring with samples. The result is greater confidence that measured absorbance values for calibration accurately represent expected reflection losses for samples under measurement and therefore enable better microtiter plate reader calibration analysis. These and other advantages of the present invention will become more apparent upon review of the following detailed description, the accompanying drawings and the appended claims.

DETAILED DESCRIPTION OF THE PRESENT INVENTION

Figure 1:
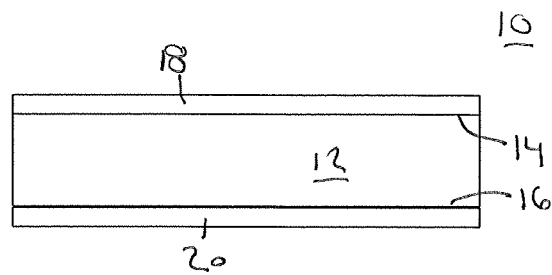
FIG. 1 is a cross sectional view of a first embodiment of the artifact apparatus of the present invention.

A first embodiment of an artifact apparatus 10 of the present invention is shown in FIG. 1. The artifact apparatus 10 is a unitary structure 12 of a transparent material, such as glass but not limited thereto, coated with specifically designed optical coating. The optical coating is selected for properties that enable mimicking of reflection losses. In the embodiments of the present invention described herein, the optical coating includes alternating layers of dielectric materials such as calcium fluoride ($CaF_2$), magnesium fluoride ($MgF_2$), zinc sulfide (ZnS), thorium fluoride ($ThF_4$), sapphire, or various other commonly used dielectric materials. These dielectric materials are deposited as alternating thin film layers (on the order of 25-50 nm thick per layer) using various surface deposition techniques such as plasma sputtering, thermal vapor deposition, and other vacuum deposition techniques commonly used and known to those skilled in the art. As noted, the unitary structure 12 is a transparent material, such as glass. In the embodiment of the invention where the unitary structure 12 is glass, the glass material can be any of a number of various types of borosilicate glass such as Schott BK7, Schott Borofloat 33, Schott BK 10, or any number of other borosilicate glass, crown glass, quartz or other glass materials commonly used and known to those skilled in the art. The glass material may also be neutral density glass material such as ND-25, ND-40 or ND-50 glass from Hoya Corporation USA (Santa Clara, Calif.), or other commonly used neutral density glass materials commonly used and known to those skilled in the art. BK7 glass available from Schott Glass Technologies Inc (Duryea, Pa.) is suitable for the purpose of the invention of FIG. 1.

The unitary structure 12 includes a first side 14 and a second side 16. The first side 14 includes a first coating 18, which is a vacuum deposited layer of dielectric material(s) of the type described above selected so that the first side 14 is able to establish a reflection loss that mimics the reflection loss at an air-liquid interface. If the test liquid to be measured by the plate reader is water, then the artifact to be used in a calibration determination will have a first coating that is selected and applied to enable the first side 14 to reflect about 2% of light incident on it. The second side 16 includes a second coating 20, which is also a vacuum deposited layer of dielectric material(s) of the type described above selected so that the second side 16 is able to establish a reflection loss that mimics the reflection loss at a bottom surface of a microtiter plate. If a polystyrene plastic microtiter plate is to be used as the test plate measured by the plate reader, then the unitary structure 12 as the artifact of the present invention to be used in a calibration determination will have a second coating 20 that is selected and applied to enable the second side 18 to reflect about 6% of light incident on it. The first coating 18 and the second coating 20 may be the same material or they may be different. If the liquid selected for calibration purposes is something other than water, such as DMSO, for example, the first coating 18 is selected and applied to establish different reflection loss characteristics consistent with that experienced with such other forms of liquid. Similarly, if the microtiter plate selected for calibration purposes is something other than polystyrene, such as glass or quartz, for example, the second coating 20 is selected and applied to establish different reflection loss characteristics consistent with that experienced with such other forms of plate bottom material.

Figure 2:
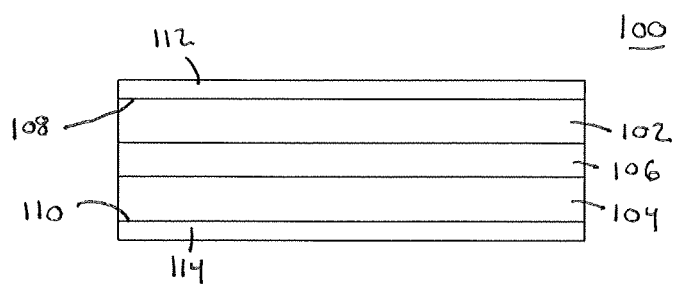
FIG. 2 is a cross sectional view of a second embodiment of the artifact apparatus of the present invention.
Figure 3:
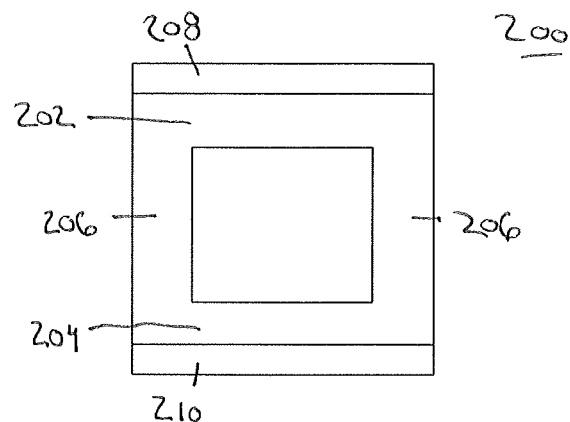
FIG. 3 is a top view of a third embodiment of the artifact apparatus of the present invention.

A second embodiment of an artifact apparatus 100 of the present invention includes multiple layers of one or more materials having some level of transparency. The one or more materials may be glass, plastic or a combination thereof. One form of this embodiment is a structure of three layers of transparent material as shown in FIG. 2. The artifact apparatus 100 of FIG. 3 is a structure including a first component 102, a second component 104 and a third component 106 positioned between the first component 102 and the second component 104. The first component 102 and the second component 104 are each a piece of glass, such as BK7 glass, or other glass such as described above. The third component 106 is a piece of neutral density glass such as Schott neutral density glass affixed between the first component 102 and the second component 104, such as by cementing or other suitable means of joining glass materials which are commonly used and known by those skilled in the art. It is to be understood that the multi-layered embodiment of the invention may be formed of two layers or more than three layers. The material selected for each layer may be the same or different and dependent upon the particular calibration interests of the user and each may or may not be formed of glass.

The first component 102 of the artifact apparatus 100 includes an exterior surface 108 and the second component 104 includes an exterior surface 110. The exterior surface 108 of the first component 102 includes a first coating 112, which is a vacuum deposited layer of dielectric material(s) of the type described above selected so that the first component 102 is able to establish a reflection loss that mimics the reflection loss at an air-liquid interface. When the liquid is water, the first coating 112 is selected and applied to enable the first component 102 to reflect about 2% of light incident on it. The exterior surface 110 of the second component 104 includes a second coating 114, which is a vacuum deposited layer of dielectric material(s) of the type described above selected so that the second component 104 is able to establish a reflection loss that mimics the reflection loss at a bottom surface of a microtiter plate. When the microtiter plate bottom is polystyrene, the second coating 114 is selected and applied to enable the second component 104 to reflect about 6% of light incident on it. The first coating 112 and the second coating 114 may be the same material or they may be different. It is to be understood that for any multi-layered version of the artifact apparatus of the present invention, a first exterior surface includes the first coating 112 and a second exterior surface includes the second coating 114. Other multi-layer compositions of the artifact may be employed, provided the first coating 112 and the second coating 114 are applied to the exterior surfaces of the multi-layer compositions. For example, an interference filter may be used as one or more of the interior layers. An interference filter layer or other type of interior layer may be used to provide an absorbance tuned to represent a test solution. There is no specific limit on the number of layers used.

A third embodiment of an artifact apparatus 200 of the present invention is shown in FIG. 3. The artifact apparatus 200 of FIG. 3 is a container having four sides, wherein opposing sides of the apparatus 200 are coated with specifically designed optical coating of the type described above. The apparatus 200, which may be a cuvette, vial or other form of container, may be formed of BK7 glass or other glass as described above or such other material suitable for this purpose. A cuvette made by Chroma Technology of Bellows Falls, Vt. is suitable for this application. The apparatus 200 may be formed in other shapes. The apparatus 200 shown in FIG. 3 includes a first side 202 and an opposing second side 204. Intermediate sides 206 may or may not include any coating. The first side 202 includes a first coating 208, which is the type of dielectric material(s) as described above selected so that the first side 202 is able to establish a reflection loss that mimics the reflection loss at an air-liquid interface. If the test liquid to be measured by the plate reader is water, then the artifact to be used in a calibration determination will have as the first coating 208 dielectric material(s) selected and applied to enable the first side 202 to reflect about 2% of light incident on it. The second side 204 includes a second coating 210, which is the type of dielectric material(s) described above selected so that the second side 204 is able to establish a reflection loss that mimics the reflection loss at a bottom surface of a microtiter plate containing the liquid. If a polystyrene plastic microtiter plate is to be used as the test plate measured by the plate reader, then the artifact to be used in the calibration determination will have as the second coating 210, dielectric material(s) selected and applied to enable the second side 204 to reflect about 6% of light incident on it. The first coating 208 and the second coating 210 may be the same material or they may be different.

The apparatus 200 formed as described may be filled with a solution having an absorbance spectrum corresponding to that of a standardized calibration solution such as, for example, the calibration solutions available from Artel, Inc., of Westbrook, Me. A plurality of such containers 200 may be employed in a calibration plate, wherein each container 200 may contain the same or a different solution. Such one or more containers 200 may then be used to measure the reflection parameters for a plate reader under test.

The artifacts 10 and 100 of FIGS. 1 and 2 may be used in a calibration process wherein an absorbance value is established for the artifact by measuring its absorbance in a spectrophotometer (horizontal or vertical beam) that is known to be calibrated. This measurement establishes a calibrated absorbance value for the artifact. The artifact with the calibrated absorbance value may then be placed in a plate reader of interest and again measured for its absorbance. The absorbance value obtained for the artifact in the plate reader is compared to the calibrated absorbance value for that artifact. A determination may then be made as to whether or not that plate reader is in conformance with tolerance specifications. If it is, then no modifications to the plate reader or calculations made based on measurements obtained using that plate reader are required. If the plate reader is out of tolerance then that may be addressed by the user. In effect, the artifact allows the user of a plate reader to maintain the plate reader in tolerance on a consistent basis. The same type of calibration process may be used with the artifact 200 of FIG. 3. Specifically in that instance, the container may be filled with a solution of interest, measured in the spectrophotometer of known calibration to obtain a calibrated absorbance value, and then placed in the plate reader under evaluation for an absorbance measurement. Deviations between the measured absorbance from the plate reader under evaluation and the calibrated absorbance value may be addressed as indicated.

With reference to U.S. Pat. No. 7,061,608 incorporated herein by reference, a method of the present invention for calibrating a plate reader under evaluation includes placing an artifact as described herein into a calibrated spectrophotometer, measuring the light absorbance of the artifact in the calibrated spectrophotometer to obtain a calibrated absorbance value for the artifact, placing the artifact in the plate reader under evaluation, measuring the light absorbance of the artifact in the plate reader under evaluation to obtain a measured light absorbance and comparing the calibrated absorbance value of the artifact with the measured light absorbance of the artifact. The artifact may be a single plate, a multi-layer composition or a container such as a cuvette. The calibrated spectrophotometer may be a horizontal or a vertical beam spectrophotometer. The result of the use of the artifact apparatus of the present invention is that the artifact is configured to appear to the plate reader as a sample to be measured in terms of the reflection losses exhibited, thereby providing a calibration corresponding to the calibration desired for sample types and sample containers of interest.

It is to be understood that various modifications may be made to the artifact apparatuses and calibration methods described herein without departing from the spirit and scope of the invention. Accordingly, other embodiments are within the scope of the claims appended hereto.

What is claimed is:

1. An artifact apparatus to aid in the calibration of a microtiter plate reader by mimicking reflection losses, the artifact apparatus comprising a unitary structure having a first side and a second side, wherein the first side includes a first coating that establishes a reflection loss of the first side that mimics reflection loss at an air-liquid interface, wherein the second side includes a second coating that establishes a reflection loss of the second side that mimics the reflection loss at a bottom surface of a microtiter plate; wherein the liquid of the air-liquid interface is water and the first coating enables the first side to reflect about 2% of light incident on it, and wherein the second coating enables the second side to reflect about 6% of light incident on it.

2. The artifact apparatus of claim 1 wherein the unitary structure is a glass structure.

3. The artifact apparatus of claim 1 wherein the first coating includes alternating layers of one or more dielectric materials.

4. The artifact apparatus of claim 1 wherein the second coating includes alternating layers of one or more dielectric materials.

5. An artifact apparatus to aid in the calibration of a microtiter plate reader by mimicking reflection losses, the artifact apparatus comprising:
   a. a first component in the form of a first structure, wherein the first component includes a first surface and a second surface;
   b. a second component in the form of a second structure, wherein the second component includes a first surface and a second surface, wherein the first structure and the second structure are joined together at their second surfaces, wherein the first surface of the first structure includes a first coating that establishes a reflection loss of the first surface of the first structure that mimics reflection loss at an air-liquid interface, and wherein the second surface of the second structure includes a second coating that establishes a reflection loss of the second surface of the second structure that mimics the reflection loss at a bottom surface of a microtiter plate;
   wherein the liquid of the air-liquid interface is water and the first coating enables the first side of the first structure to reflect about 2% of light incident on it; and
   wherein the second coating of the second structure enables the second side to reflect about 6% of light incident on it.

6. The artifact apparatus of claim 5 wherein the first structure and the second structure are glass structures.

7. The artifact apparatus of claim 5 further comprising one or more additional components affixed between the first component and the second component.

8. The artifact apparatus of claim 7 wherein one or more of the one or more additional components is a neutral density glass structure.

9. The artifact apparatus of claim 7 wherein one or more of the one or more additional components is an interference filter.

10. The artifact apparatus of claim 5 wherein the first coating includes alternating layers of one or more dielectric materials.

11. The artifact apparatus of claim 5 wherein the second coating includes alternating layers of one or more dielectric materials.

12. An artifact apparatus to aid in the calibration of a microtiter plate reader by mimicking reflection losses, the artifact apparatus comprising a container having a first side and an opposing second side, wherein the first side includes a first coating that establishes a reflection loss of the first side that mimics reflection loss at an air-liquid interface, wherein the second side includes a second coating that establishes a reflection loss of the second side that mimics the reflection loss at a bottom surface of a microtiter plate, wherein the liquid of the air-liquid interface is water and the first coating enables the first side to reflect about 2% of light incident on it, and wherein the second coating enables the second side to reflect about 6% of light incident on it.

13. The artifact apparatus of claim 12 wherein the first coating includes alternating layers of one or more dielectric materials.

14. The artifact apparatus of claim 12 wherein the second coating includes alternating layers of one or more dielectric materials.

15. A method of the present invention for calibrating a microtiter plate reader using an artifact to mimic reflection losses, the method comprising the steps of:

a. placing an artifact into a calibrated spectrophotometer, wherein the artifact includes a first side and a second side, wherein the first side includes a first coating selected so that the first side is able to establish a reflection loss that mimics reflection loss at an air-liquid interface, wherein the second side includes a second coating selected so that the second side is able to establish a reflection loss that mimics the reflection loss at a bottom surface of a microtiter plate, wherein the second side includes a second coating that establishes a reflection loss of the second side that mimics the reflection loss at a bottom surface of a microtiter plate, wherein the liquid of the air-liquid interface is water and the first coating enables the first side to reflect about 2% of light incident on it, and wherein the second coating enables the second side to reflect about 6% of light incident on it;

b. measuring light absorbance of the artifact in the calibrated spectrophotometer to obtain a calibrated absorbance value for the artifact;

c. placing the artifact in a plate reader under evaluation;

d. measuring the light absorbance of the artifact in the plate reader under evaluation to obtain a measured light absorbance; and e. comparing the calibrated absorbance value of the artifact with the measured light absorbance of the artifact.

16. The method of claim 15 wherein the artifact is a unitary structure.

17. The method of claim 15 wherein the artifact is a multi-layer structure.

18. The method of claim 15 wherein the artifact is a container.

19. The method of claim 15 wherein the calibrated spectrophotometer is a horizontal or a vertical beam spectrophotometer.

* * * * *